(12) United States Patent
Haarala et al.

(10) Patent No.: US 9,381,037 B2
(45) Date of Patent: Jul. 5, 2016

(54) CATHETER TUNNELING SYSTEMS, INSTRUMENTS AND METHODS

(71) Applicant: Covidien LP, Mansfield, MA (US)

(72) Inventors: Brett Haarala, Framingham, MA (US); Richard Braga, North Easton, MA (US)

(73) Assignee: Covidien LP, Mansfield, MA (US)

( * ) Notice: Subject to any disclaimer, the term of this patent is extended or adjusted under 35 U.S.C. 154(b) by 227 days.

(21) Appl. No.: 14/066,736

(22) Filed: Oct. 30, 2013

(65) Prior Publication Data

US 2014/0114289 A1  Apr. 24, 2014

Related U.S. Application Data

(62) Division of application No. 12/041,422, filed on Mar. 3, 2008, now Pat. No. 8,574,192.

(60) Provisional application No. 60/904,462, filed on Mar. 2, 2007.

(51) Int. Cl.
 A61B 17/34 (2006.01)
 A61M 25/01 (2006.01)
 A61B 17/32 (2006.01)

(52) U.S. Cl.
 CPC .......... *A61B 17/3415* (2013.01); *A61B 17/3417* (2013.01); *A61M 25/0102* (2013.01); *A61M 25/0194* (2013.01); *A61B 2017/320056* (2013.01)

(58) Field of Classification Search
 CPC ........... A61B 17/3415; A61B 17/3417; A61B 2017/320056; A61M 25/0102; A61M 25/0194
 See application file for complete search history.

(56) References Cited

U.S. PATENT DOCUMENTS

| | | | |
|---|---|---|---|
| 4,299,228 A | 11/1981 | Peters | |
| 4,490,136 A | 12/1984 | Ekbladh et al. | |
| 4,674,496 A | 6/1987 | Svadjian et al. | |
| 4,705,041 A | 11/1987 | Kim | |
| 4,819,694 A | 4/1989 | Jiang | |
| 4,832,687 A * | 5/1989 | Smith, III | 604/506 |
| 5,059,170 A | 10/1991 | Cameron | |
| 5,129,891 A | 7/1992 | Young | |
| 5,207,643 A | 5/1993 | Davis | |
| 5,209,723 A | 5/1993 | Twardowski et al. | |
| 5,279,597 A | 1/1994 | Dassa et al. | |
| 5,358,506 A | 10/1994 | Green et al. | |
| 5,405,320 A | 4/1995 | Twardowski et al. | |
| 5,478,318 A | 12/1995 | Yoon | |
| 5,505,714 A | 4/1996 | Dassa et al. | |
| 5,509,897 A | 4/1996 | Twardowski et al. | |
| 5,562,618 A | 10/1996 | Cai et al. | |

(Continued)

OTHER PUBLICATIONS

"Aspira* Pleural Drainage System", Bard Access Systems, Inc., Salt Lake City, Utah, Instruction Manual dated Oct. 2007.

(Continued)

*Primary Examiner* — Bradley Osinski

(57) ABSTRACT

An instrument for facilitating insertion of a catheter through a subcutaneous tunnel includes a tunneling stylet defining a longitudinal axis and having leading and trailing ends, a bifurcated segment adjacent the leading end of the tunneling stylet and a releasable cover releasably mountable to the leading end of the tunneling stylet to substantially enclose the bifurcated segment. The bifurcated segment includes first and second elements adapted for reception within respective lumens of a catheter.

10 Claims, 14 Drawing Sheets

(56) References Cited

U.S. PATENT DOCUMENTS

| | | | |
|---|---|---|---|
| 5,613,945 A | 3/1997 | Cai et al. | |
| 5,624,413 A | 4/1997 | Markel et al. | |
| 5,632,729 A | 5/1997 | Cai et al. | |
| 5,637,102 A | 6/1997 | Tolkoff et al. | |
| 5,718,678 A | 2/1998 | Fleming, III | |
| 5,743,873 A | 4/1998 | Cai et al. | |
| 5,944,732 A | 8/1999 | Raulerson et al. | |
| 6,099,519 A | 8/2000 | Olsen et al. | |
| 6,113,572 A | 9/2000 | Gailey et al. | |
| 6,126,631 A | 10/2000 | Loggie | |
| 6,423,053 B1 | 7/2002 | Lee | |
| 6,453,185 B1 | 9/2002 | O'Keefe | |
| 6,638,242 B2 | 10/2003 | Wilson et al. | |
| D498,844 S | 11/2004 | Diamond et al. | |
| 6,858,019 B2 | 2/2005 | McGuckin, Jr. et al. | |
| 6,872,198 B1 | 3/2005 | Wilson et al. | |
| 6,911,014 B2 | 6/2005 | Wentling et al. | |
| 6,916,051 B2 | 7/2005 | Fisher | |
| 6,921,396 B1 | 7/2005 | Wilson et al. | |
| 6,939,328 B2 | 9/2005 | Raulerson | |
| 6,969,381 B2 | 11/2005 | Voorhees | |
| 6,979,339 B2 | 12/2005 | Bishop et al. | |
| 7,008,395 B1 | 3/2006 | Loggie | |
| 7,087,071 B2 | 8/2006 | Nicholas et al. | |
| 7,128,734 B1 | 10/2006 | Wilson et al. | |
| 7,144,409 B2 | 12/2006 | Aranyi | |
| 7,163,531 B2 | 1/2007 | Seese et al. | |
| 7,261,708 B2 | 8/2007 | Raulerson | |
| 7,300,430 B2 | 11/2007 | Wilson et al. | |
| 8,574,192 B2 | 11/2013 | Haarala et al. | |
| 2004/0034324 A1 | 2/2004 | Seese et al. | |
| 2004/0065333 A1 | 4/2004 | Wilson et al. | |
| 2004/0167478 A1 | 8/2004 | Mooney et al. | |
| 2004/0171997 A1 | 9/2004 | Wilson et al. | |
| 2004/0176739 A1 | 9/2004 | Stephens et al. | |
| 2005/0085765 A1 | 4/2005 | Voorhees | |
| 2005/0107770 A1 | 5/2005 | Schweikert et al. | |
| 2005/0137580 A1 | 6/2005 | Raulerson et al. | |
| 2005/0187535 A1* | 8/2005 | Wilson et al. | 604/523 |
| 2005/0209583 A1 | 9/2005 | Powers et al. | |
| 2005/0209584 A1 | 9/2005 | Rome | |
| 2005/0228364 A1* | 10/2005 | Braga | 606/1 |
| 2005/0256461 A1 | 11/2005 | DiFiore et al. | |
| 2005/0261665 A1 | 11/2005 | Voorhees | |
| 2006/0009783 A1 | 1/2006 | Rome et al. | |
| 2006/0015086 A1 | 1/2006 | Rasmussen et al. | |
| 2006/0015130 A1 | 1/2006 | Voorhees et al. | |
| 2006/0095062 A1 | 5/2006 | Stephens | |
| 2006/0135949 A1 | 6/2006 | Rome et al. | |
| 2006/0224110 A1 | 10/2006 | Scott et al. | |
| 2006/0276773 A1 | 12/2006 | Wilson et al. | |
| 2007/0016167 A1 | 1/2007 | Smith et al. | |
| 2007/0049960 A1 | 3/2007 | Stephens et al. | |
| 2007/0060866 A1 | 3/2007 | Raulerson et al. | |
| 2007/0078396 A1 | 4/2007 | Feeley et al. | |
| 2007/0260221 A1 | 11/2007 | Chesnin | |
| 2007/0265597 A1 | 11/2007 | Schweikert et al. | |
| 2007/0282274 A1 | 12/2007 | Chesnin | |
| 2008/0009832 A1 | 1/2008 | Barron et al. | |
| 2008/0086161 A1 | 4/2008 | Massengale et al. | |
| 2008/0097409 A1 | 4/2008 | Stephens | |
| 2008/0214992 A1 | 9/2008 | Haarala et al. | |

OTHER PUBLICATIONS

European Patent Search Report EP 11 18 3344 dated Dec. 21, 2011.

* cited by examiner

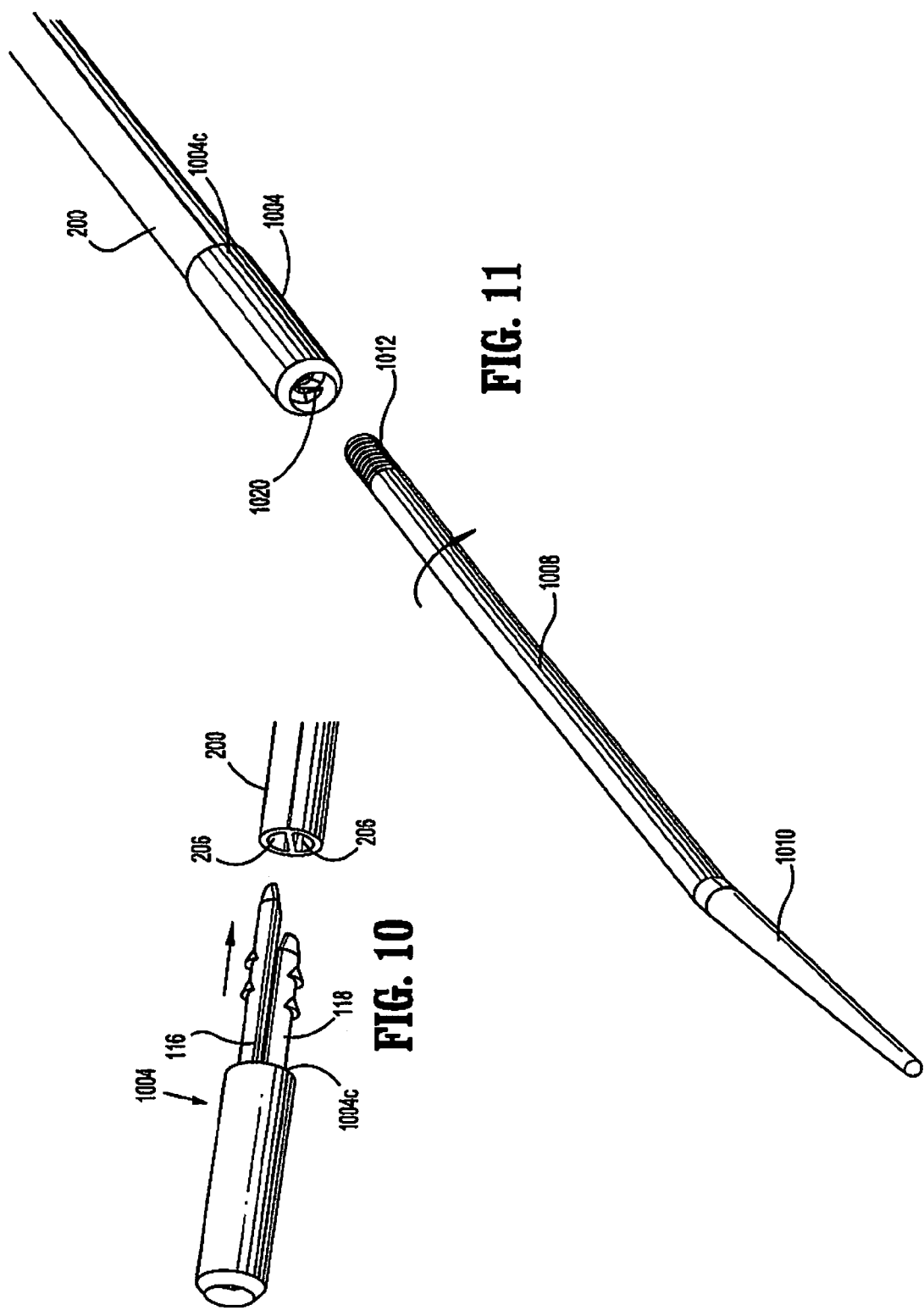

CATHETER TUNNELING SYSTEMS, INSTRUMENTS AND METHODS

CROSS REFERENCE TO RELATED APPLICATION(S)

This application is a divisional of U.S. patent application Ser. No. 12/041,422 filed on Mar. 3, 2008, which issued as U.S. Pat. No. 8,574,192 on Nov. 5, 2013, and which claims priority to, and the benefit of, U.S. Provisional Application Ser. No. 60/904,462 filed on Mar. 2, 2007. The entire contents of each of these applications are incorporated by reference herein.

BACKGROUND

1. Technical Field

The present disclosure relates generally to catheter tunneling systems, instruments and methods and, more particularly, relates to a catheter tunneling instrument utilized in connection with a hemodialysis procedure.

2. Description of the Related Art

Catheters are flexible medical instruments intended for the withdrawal and introduction of fluids relative to body cavities, ducts, and vessels. Catheter instrumentation may have particular application in a hemodialysis procedure where blood is withdrawn from a blood vessel for treatment, and subsequently returned to the blood vessel for circulation. Known hemodialysis catheters include multiple lumens, such as dual lumen or triple-lumen catheters, permitting bi-directional fluid flow within the catheter whereby one lumen is dedicated for withdrawal of blood and the other lumen is dedicated for returning the treated blood to the vessel. During an exemplary hemodialysis procedure, a multiple lumen catheter is inserted into a body and blood is withdrawn through an arterial lumen of the catheter. The removed blood is directed to a hemodialysis unit which dialyzes, or purifies, the blood to remove waste, and toxins. The dialyzed blood is returned to the patient through a venous lumen of the catheter.

Various techniques are employed for the insertion of hemodialysis catheters including, e.g., with the use of guidewires, introduction stylets or the like. Some of these known techniques include subcutaneous tunneling methodologies where a subcutaneous tunnel is formed between two spaced openings in the skin with the use of a trocar or the like. The catheter end is attached to the trocar and pulled though the tunnel to expose the catheter which is subsequently inserted into, e.g., the jugular vein and routed to the heart.

SUMMARY

Accordingly, the present disclosure is directed to an instrument for facilitating insertion of a catheter through a subcutaneous tunnel. The instrument includes a tunneling stylet defining a longitudinal axis and having leading and trailing ends, a bifurcated segment adjacent the leading end of the tunneling stylet and having first and second elements adapted for reception within respective lumens of a catheter and a releasable cover releasably mountable to the leading end of the tunneling stylet to at least partially enclose the bifurcated segment. The instrument may further include a dilation member releasably mountable to the leading end of the tunneling stylet in the absence of the releasable cover. The dilation member is dimensioned to generally increase an internal dimension of the subcutaneous tunnel. The bifurcated segment may be releasably mountable to the tunneling stylet.

The first and second elements of the bifurcated segment each may include an outer peripheral rib dimensioned to facilitate gripping engagement with an internal surface of a respective lumen of the catheter. The first and second elements of the bifurcated segment may include a plurality of spaced outer peripheral ribs. At least one of the peripheral ribs has a tapered profile for facilitating insertion of the first and second elements within respective lumens of the catheter. The first element of the bifurcated segment may have a first longitudinal length and the second element of the bifurcated segment may have a second longitudinal length with the first length being greater than the second length to facilitate insertion within the catheter.

The leading end of the tunneling stylet may define a collar located proximally relative to the bifurcated segment. The leading end also may include an external thread adjacent the collar for facilitating secure engagement to the releasable cover. The leading end may be arranged at an oblique angle with respect to the longitudinal axis of the tunneling stylet.

The instrument may include a handle positioned adjacent the trailing end of the tunneling stylet and adapted to facilitate engagement by a clinician. The handle may include an offset segment and a gripping segment. The offset segment may be arranged at an oblique angle with respect to the longitudinal axis of the tunneling stylet to displace the gripping segment from the longitudinal axis.

In another embodiment, an instrument for facilitating insertion of a catheter through a subcutaneous tunnel includes a tunneling stylet defining a longitudinal axis and having leading and trailing ends and a bifurcated segment adjacent the leading end of the tunneling stylet. The bifurcated segment includes first and second elements adapted for reception within respective lumens of a catheter. The first element and the second element define respective first and second longitudinal lengths. The first longitudinal length is greater than the second longitudinal length to assist in positioning within the catheter. The bifurcated segment may be securely connected to the tunneling stylet or releasably connected to the tunneling stylet.

In another embodiment, an instrument for facilitating insertion of a catheter through a subcutaneous tunnel includes a tunneling stylet having first and second segments, a bifurcated segment releasably connectable to the first segment and a dilation member releasably connectable to the first segment in the absence of the bifurcated segment. The first segment of the tunneling stylet defines a longitudinal axis along at least a portion of a length thereof and the second segment is dimensioned for passage through tissue. The bifurcated segment includes first and second mounting elements adapted for reception within respective lumens of the catheter. The dilation member is dimensioned to generally increase an internal dimension of the subcutaneous tunnel. The first segment of the tunneling stylet and the bifurcated segment may include cooperative threaded portions for establishing a releasable connection therebetween. The first segment of the tunneling stylet and the dilation member may include cooperative threaded portions for establishing a releasable connection therebetween.

A method for implanting a catheter for use in a hemodialysis procedure is also disclosed. The method includes the steps of:

providing a tunneling instrument including a tunneling stylet having leading and trailing ends, a catheter connector segment adjacent the trailing end and a releasable cover adjacent the leading end and at least partially mounted about the connector segment;

accessing the venous system of a subject with one end of a hemodialysis catheter;

advancing the leading end of the tunneling stylet with mounted releasable cover subcutaneously through the tissue in a first direction to at least partially expose the releasable cover through a first tissue opening;

removing the releasable cover from the catheter connector segment;

fluidly connecting the catheter connector segment to a second catheter end of the hemodialysis catheter;

retracting the tunneling stylet and the second catheter end in a second direction opposite of the first direction to expose the second catheter end through a second tissue opening; and connecting the second catheter end to a hemodialysis apparatus.

In the alternative, a method for implanting a catheter for use in a hemodialysis procedure, includes the steps of:

providing a tunneling instrument including a tunneling stylet having leading and trailing ends and a catheter connector segment releasably connected to the trailing end;

accessing the venous system through a first tissue opening of a subject with a first end of a hemodialysis catheter;

mounting the catheter connector segment to a second end to substantially seal a lumen within the catheter;

releasably connecting the tunneling stylet to the catheter connector segment;

advancing the leading end of the tunneling stylet subcutaneously through the tissue to expose the second catheter end through a second tissue opening; and connecting the second catheter end to a hemodialysis apparatus.

BRIEF DESCRIPTION OF THE DRAWINGS

Preferred embodiments of the disclosure will be better understood with reference to the accompanying drawings wherein:

FIG. 1A is an enlarged perspective view of the area of detail indicated in FIG. 1 illustrating the bifurcated segment and the releasable cover;

FIG. 2A is an enlarged perspective view of the area of detail indicated in FIG. 2;

FIG. 3A is an enlarged perspective view of the area of detail indicated in FIG. 3;

FIG. 4A is an enlarged perspective view of the area of detail indicated in FIG. 4;

FIG. 10 is a perspective view illustrating mounting of the releasable bifurcated segment to the catheter;

FIG. 11 is a perspective view illustrating mounting of the releasable bifurcated segment to the tunneling stylet;

FIG. 13 is a perspective view of an alternate embodiment of the instrument of FIG. 8;

DETAILED DESCRIPTION OF THE EMBODIMENTS

The exemplary embodiments of the tunneling instruments, systems and associated methods of use have several applications. For instance, a clinician may utilize the disclosed tunneling instrument to facilitate the insertion of a catheter in a subcutaneous tunnel during a hemodialysis procedure. It is envisioned, however, that the present disclosure may be employed in a wide range of applications including surgical, diagnostic and related treatments of diseases and body ailments of a subject.

In the discussion that follows, the term "proximal" or "trailing" refers to the portion of a structure that is closer to a clinician, while the term "distal" or "leading" refers to the portion that is farther from the clinician. As used herein, the term "subject" refers to a human patient or other animal. The term "clinician" refers to a doctor, nurse or other care provider and may include support personnel.

The following discussion includes a description of the tunneling systems followed by a description of exemplary associated methods of using the tunneling systems in insertion of a hemodialysis catheter. The methods contemplated include a variety of tunneling procedures, including, but, not limited to reverse tunneling procedures and ante-grade tunneling procedures. However, those skilled in the art will appreciate the catheter has many other applications in addition to dialysis applications.

Figure 1:
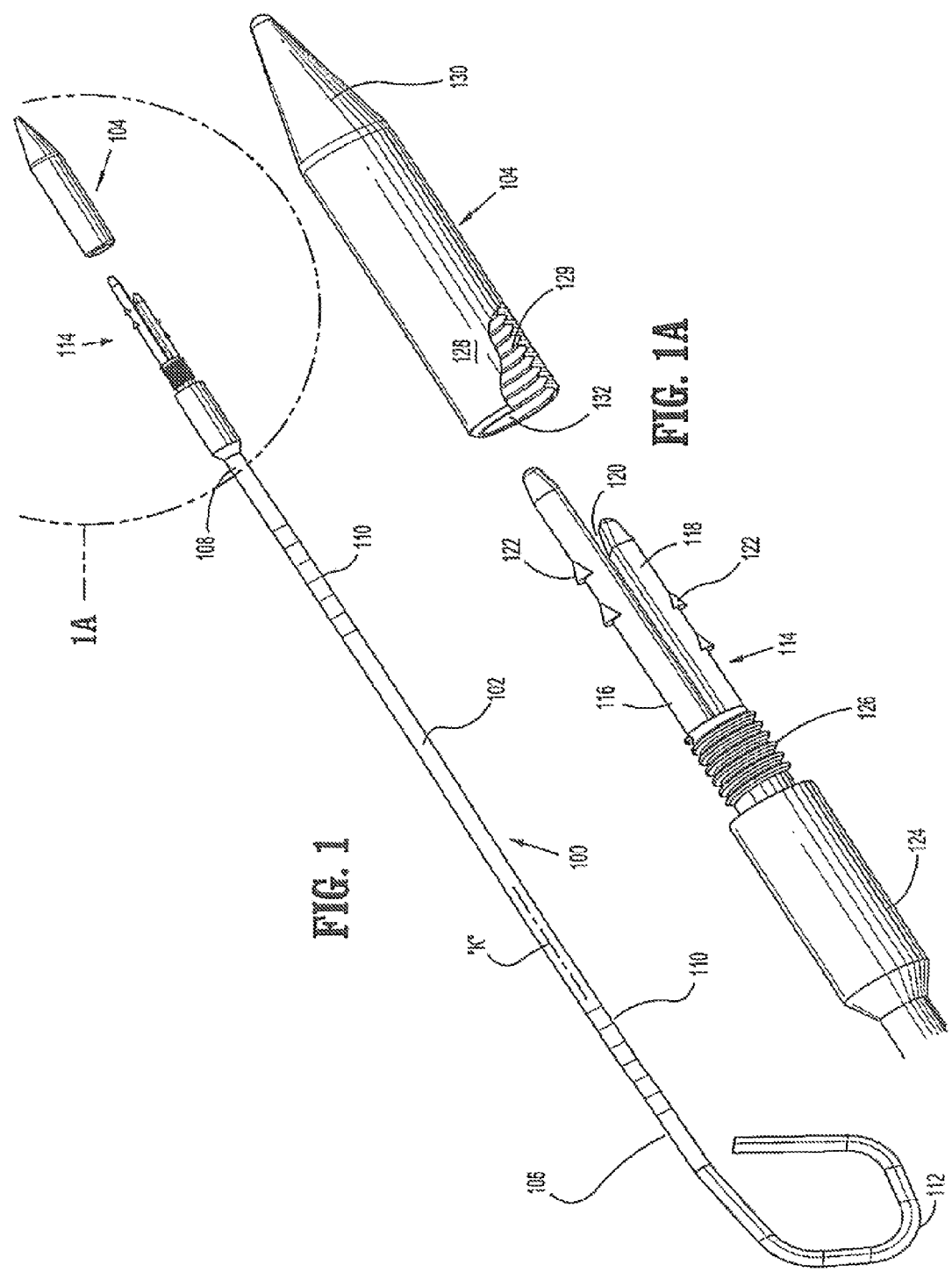
FIG. 1 is a perspective of a tunneling instrument in accordance with the principles of the present disclosure illustrating the tunneling stylet, the bifurcated segment and the releasable cover.

Referring now to the drawings wherein like components are designated by like reference numerals throughout the several views, FIGS. 1-1A illustrate the tunneling instrument in accordance with the principles of the present disclosure. Tunneling instrument 100 includes tunneling or insertion stylet 102 and releasable cover 104, which is releasably mountable to the tunneling stylet 102. Releasable cover 104 will be discussed in greater detail hereinbelow. Tunneling stylet 102 defines longitudinal axis "k" and has trailing and leading ends 106, 108, respectively. Tunneling stylet 102 is fabricated from a biocompatible metal such as stainless steel or titanium or a suitable polymeric material. Tunneling stylet 102 may be adapted to bend to facilitate advancement through the subcutaneous tissue. For example, tunneling stylet 102 may be bent or altered in configuration to assist in manipulation through the subcutaneous tissue. Tunneling stylet 102 may incorporate various indicia or gradation markings 110 along its length to assist to clinician in determining the depth of insertion of the tunneling stylet 102. Gradation markings 110 may also consist of various radiopaque markings that are detectable during an x-ray scanning procedure.

Trailing end 106 may include handle 112 which is dimensioned for manipulation by the clinician. Handle 112 may incorporate any arrangement suitable to enhance gripping engagement by the clinician. In one embodiment, handle 112 includes a loop. The configuration of the loop of handle 112 enables the clinician to position his fingers within the loop when pulling tunneling stylet 102 through a subcutaneous tunnel. Handle 112 may incorporate an ergonomic arrangement or any other arrangement suitable for grasping engagement by a clinician.

With continued reference to FIGS. 1-1A, tunneling stylet 102 includes catheter mounting or bifurcated segment 114 adjacent leading end 108. Bifurcated segment 114 incorporates first and second mounting elements 116,118 which are radially spaced to define gap 120 therebetween. First and second mounting elements 116,118 are dimensioned to be received within respective lumens of a catheter as will be discussed hereinbelow. First mounting element 116 defines a length which is greater than a corresponding length of a second mounting element 118. This staggered length arrangement may facilitate insertion of first and second mounting elements 116, 118 within the lumens of the catheter. First and second mounting elements 116, 118 each may include one or more locking ribs 122 on their outer surfaces. Locking ribs 122 are dimensioned to facilitate engagement (e.g., frictional) with internal surfaces defining the lumens of the catheter. Locking ribs 122 of respective first and second mounting elements 116, 118 may be longitudinally spaced from each other as shown in FIG. 1A. In one arrangement, locking ribs 122 are tapered so as to gradually increase the effective cross-sectional dimensions of respective first and second mounting elements 116, 118 towards trailing end 106 of tunneling stylet 102 to facilitate insertion of the first and second mounting elements 116, 118 within the lumens of the catheter.

Leading end 106 further defines collar 124 proximal of bifurcated segment 114 and mounting means in the form of external thread 126 between the collar 124 and the bifurcated segment 114.

Tunneling stylet 102, including trailing and leading ends 106,108 and bifurcated segment 114, may be integrally formed as a single unit. Alternatively, tunneling stylet 102 may be constructed of separable components connectable to each other via various connection means appreciated by one skilled the art.

Figure 2:
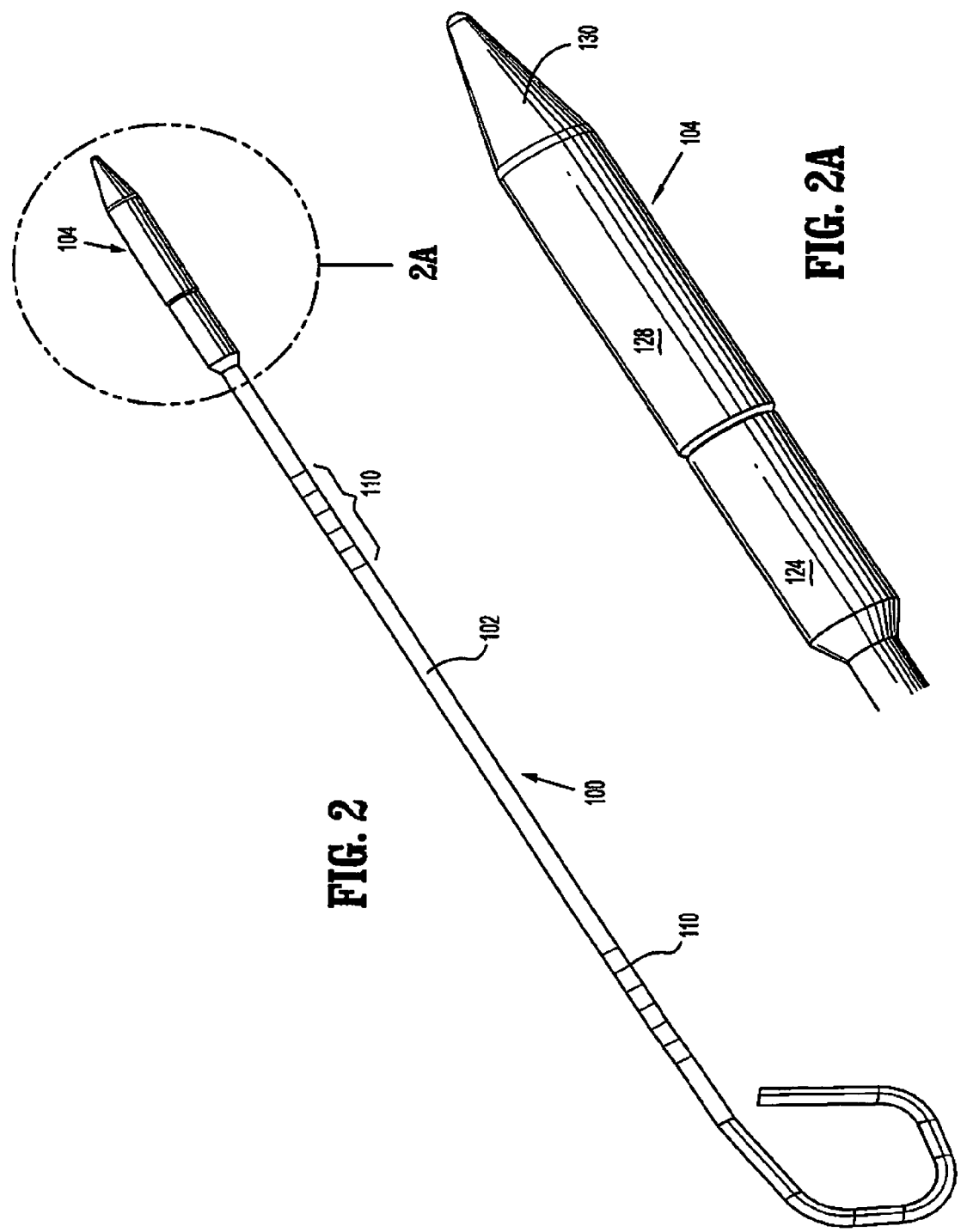
FIG. 2 is a perspective view of the tunneling instrument of FIG. 1 with the releasable cover mounted to the tunneling stylet.

Referring now to FIGS. 1-2, cover 104 will be discussed. Cover 104 includes trailing section 128 and leading section 130. Trailing section 128 is adapted to be positioned over bifurcated segment 114 to substantially enclose the bifurcated segment 114. Trailing section 128 may be generally cylindrical in configuration. In one embodiment, trailing section 128 includes a single lumen 132 for reception of both first and second mounting elements 116, 118 of bifurcated segment 114. In the alternative, trailing section 128 may include two distinct lumens (not shown) for receiving first and second mounting elements 116, 118 respectively. Trailing section 128 may incorporate an internal thread 129 as shown in the partial removed portions of cover 104 depicted in FIG. 1A. Internal thread 129 cooperates with external thread 126 of tunneling stylet 102 to releasably secure cover 104 to insertion stylet 102. However, the internal thread is not needed to achieve the objectives of the present disclosure. Leading section 130 of cover 104 is generally tapered or frusto-conical in configuration to facilitate passage of cover 104 and insertion stylet 102 through the subcutaneous tissue.

Cover 104 may be fabricated from a biocompatible metal or polymeric material as discussed hereinabove in connection with tunneling stylet 102. Cover 104 may also be fabricated from a suitable elastomeric material capable of resiliently stretching when positioned over bifurcated segment 114.

FIGS. 2-2A illustrate cover 104 mounted to tunneling stylet 102. As shown, trailing section 128 of cover 104 may engage collar 124 of tunneling stylet 102 to ensure that no tissue or fluids may enter beneath the cover 104 and contact bifurcated segment 114. Trailing section 128 may abut collar 124 or be at least partially positioned over the collar 124. In the mounted condition of cover 104, locking ribs 122 may engage the internal surface of the cover 104 to facilitate releasable securement of the cover 104 relative to insertion stylet 102. Internal thread 129 (if provided) of cover 104 may threadably engage external thread 126 of tunneling stylet 102. Alternatively, if internal thread 129 is not incorporated into cover 104, external thread 126 may engage internal surfaces within trailing section 128 of cover 104. External thread 126 may be replaced with a knurling, roughened surfaces, irregularities or the like to engage the internal surfaces of trailing section 128.

Figure 3:
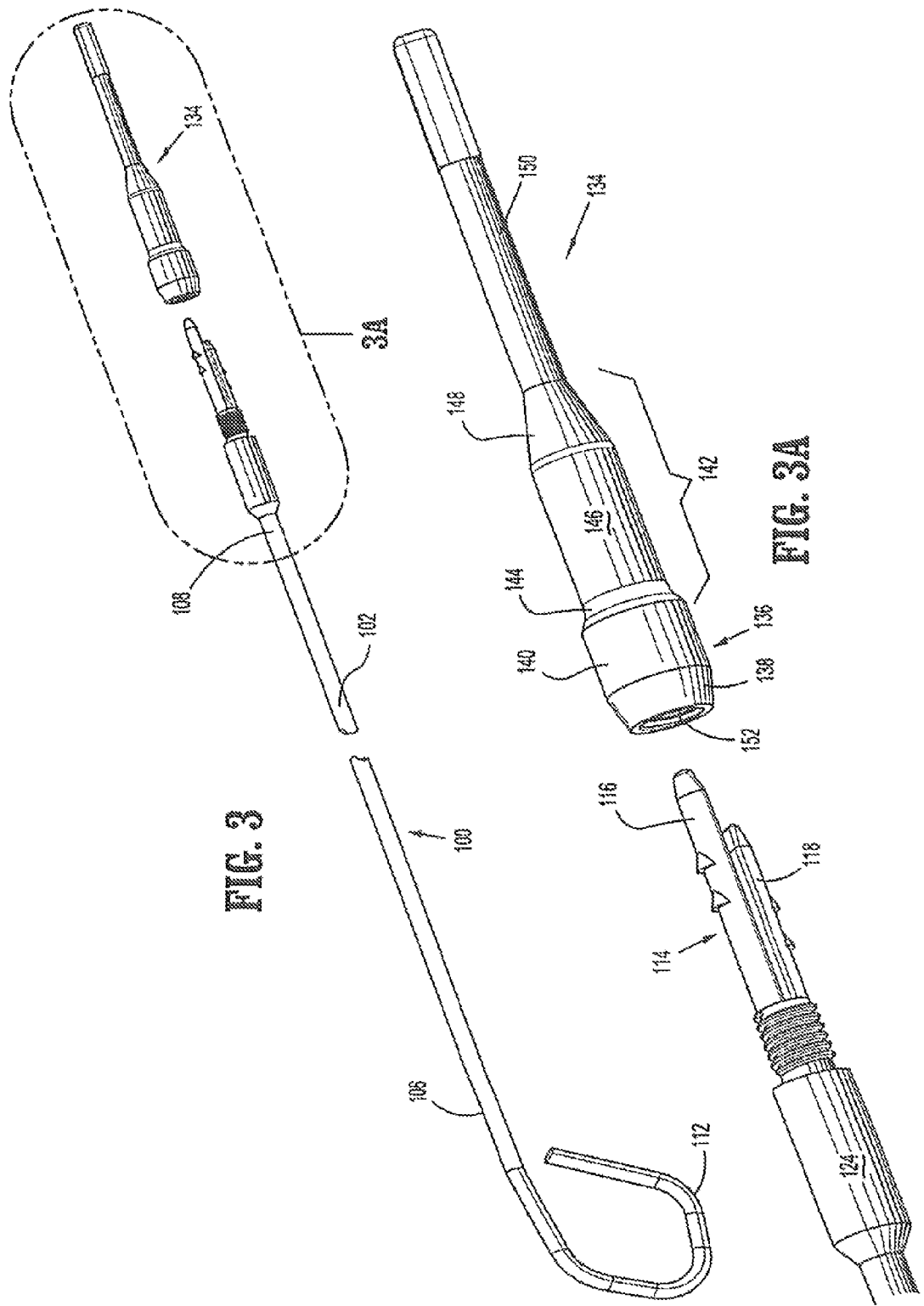
FIG. 3 is a perspective view of the tunneling instrument of FIG. 1 and an optional dilation member releasably mountable to the tunneling stylet.

Referring now to FIGS. 3-3A, tunneling instrument 100 may further include dilator element 134. Dilator element 134 is adapted for releasable mounting to tunneling stylet 102. Dilator element 134 may be incorporated to dilate a portion of the subcutaneous tunnel to, e.g., create an internal shelf within the subcutaneous tunnel to thereby facilitate placement of a cuff connected to the external surface of the catheter. Dilator element 134 includes trailing segment 136 incorporating tapered segment 138 and cylindrical segment or collar 140. Dilator element 134 further includes intermediate segment 142 having tapered segment 144, cylindrical segment 146 and tapered segment 148. Dilator element 134 further includes leading segment 150 which is generally cylindrical in configuration. Trailing segment 136 may define an outer diameter or dimension which is greater than a corresponding outer diameter or dimension of collar 124 of tunneling stylet 102. The significance of this dimensioning will be discussed in greater detail hereinbelow.

Dilator element 134 may incorporate internal threads 152 which cooperate with external threads 126 of tunneling stylet 102 to securely releasably connect the dilator element 134 to the tunneling stylet 102. Other means for releasably connecting dilator element 134 to tunneling stylet 102 are also envisioned including bayonet coupling, snap lock, a frictional relationship lock of the like, or any other suitable connecting apparatus.

Figure 4:
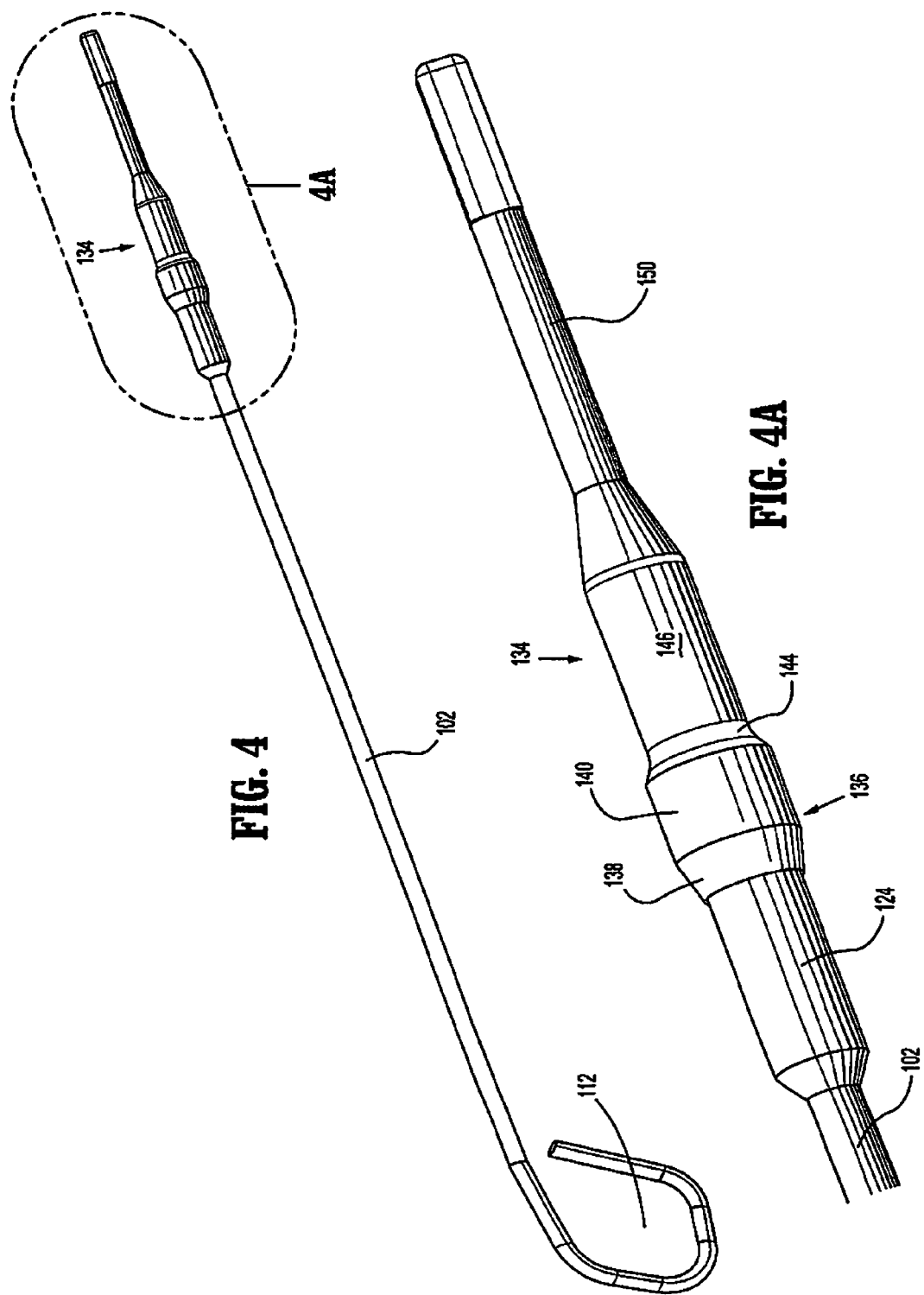
FIG. 4 is a perspective view of the tunneling instrument illustrating the dilation member mounted to the tunneling stylet.

FIGS. 4-4A illustrate dilator element 134 mounted to tunneling stylet 102. As shown, tapered segment 138 gradually tapers from cylindrical segment 140 to define an outer diameter or dimension which generally approximates the outer diameter or dimension of collar 124 of tunneling stylet 102. Thus, by virtue of this arrangement, tapered segment 138 may gradually increase the internal dimension of the subcutaneous tunnel to at least the maximum outer dimension of the tapered segment 138 (corresponding to the dimension of cylindrical segment 140) while insertion stylet 102 is pulled through the subcutaneous tunnel.

The use of tunneling instrument 100 will now be discussed in terms of a reverse tunneling procedure in connection with hemodialysis treatment. The application will be discussed in terms of deploying a catheter through the right jugular vein for positioning within the right atrium and creating a tunnel. In one application, catheter may be a dual lumen catheter including two generally D-shaped lumens separated by septum wall. For example, suitable catheters include the Mahurkar® dual and triple lumen catheters available from Covidien. Other catheters are also envisioned including triple lumen catheters, coaxial lumen catheters or any other suitable catheter having application in the removal and return of fluids to and from the subject in, e.g., a hemodialysis procedure. The catheter may be fabricated from a suitable elastomeric, thermoplastic or polymeric material, and manufacturing through known extrusion or molding techniques or any other conventionally acceptable methodology. The catheter 200 is relatively flexible and may be capable of some deformation.

As appreciated, the catheter may be implanted in the right atrium via the left jugular vein, the right atrium through the right subclavian vein, the right atrium through the left subclavian vein, or implanted in the femoral vein of the subject.

Figure 5:
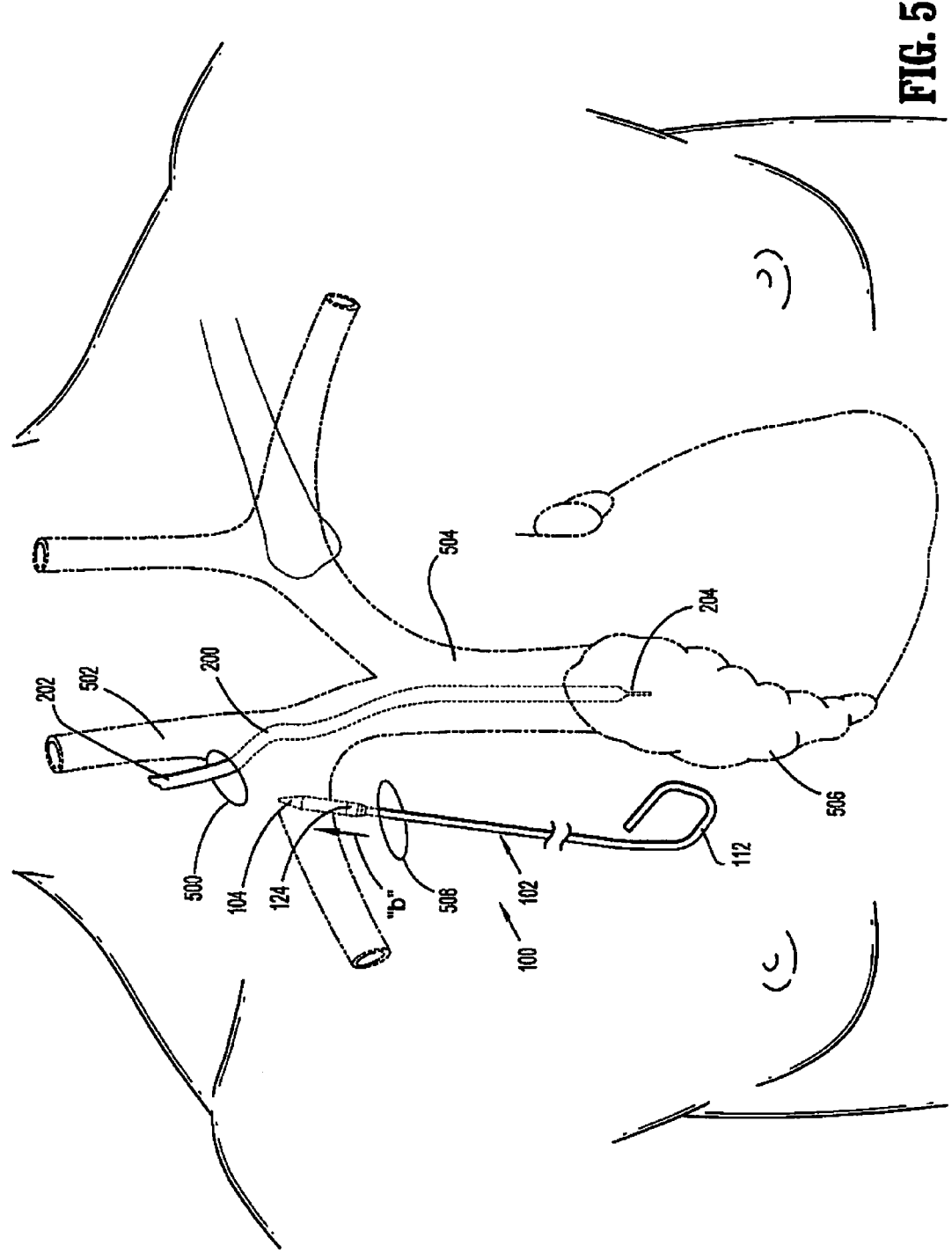
FIG. 5 is a view of the chest area of a patient illustrating a methodology use of the tunneling instrument through a reverse tunneling procedure.

Referring now to FIG. 5, the internal jugular vein 502 is located and punctured with an introducer needle and a guidewire is inserted into the jugular vein 502 using known techniques. The needle is removed and the opening 500 from the skin to the jugular vein 502 is enlarged adjacent to and along the pathway of the guidewire into the jugular vein 502 so that a catheter may be inserted in to the jugular vein 502. The leading end of a catheter 200 is then inserted in to the opening 500, through the jugular vein 502, the superior vena cava 504, and into the right atrium 506. The positioning of the leading end 204 of catheter 200 may be confirmed with an x-ray if desired. The trailing end 202 of the catheter may extend from the venotomy site 500.

Once the leading or distal end 204 of catheter 200 is in position, attention is directed to preparing the subcutaneous tunnel. A small exit site or opening 508 is made adjacent the chest wall below the venotomy site 500 to define the base of the subcutaneous tunnel. Thereafter, tunneling stylet 102 with releasable cover 104 mounted thereto in the condition depicted in FIGS. 2-2A is introduced into the subject through the exit site 508 and advanced toward the venotomy site 500 (in the direction of arrow "B") to create a subcutaneous tunnel. Releasable cover 104 of tunneling instrument 100 is designed with optimized geometry to permit effective dissection of subcutaneous tissue as it is advanced toward the venotomy site 500. Once releasable cover 104 is exposed or extends from the venotomy site 500, the releasable cover 104 is removed from tunneling stylet 102. Thereafter, optionally, dilator element 134 may be releasably secured to tunneling stylet 102 via any of the aforementioned connection means (e.g., through threaded cooperation of external threads 126 of tunneling stylet 102 and internal threads 152 of dilator element 134), and the tunneling stylet 102 is retracted or pulled back a predetermined distance within the created subcutaneous tunnel. This activity consequently causes a portion of the subcutaneous tunnel adjacent the venotomy site 500 to be dilated due to tapered segment 138 of dilator element 134 engaging the internal tissue. The predetermined distance will generally correspond to the desired location of the cuff attached to the catheter 200. The juncture of the internal tissue dilated by dilator element 134 and the remaining portion of the subcutaneous tunnel defines a ledge or shelf to accommodate the cuff of the catheter. Once the shelf is created, tunneling stylet 102 is again advanced towards the venotomy site 500 to at least partially expose dilator element 134. Dilator element 134 is thereafter removed from tunneling stylet 102.

Figure 6:
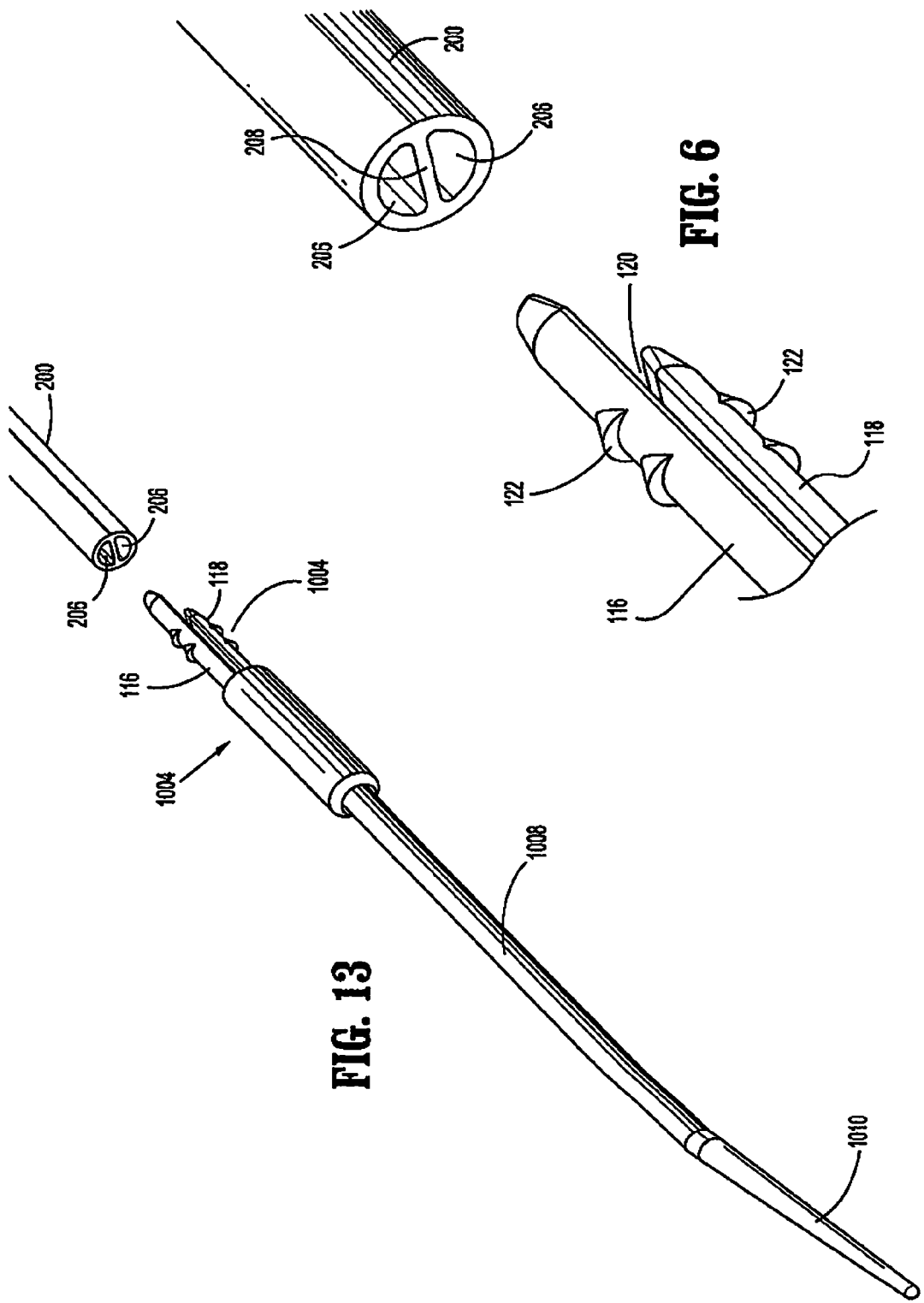
FIG. 6 is an enlarged perspective view illustrating the tunneling stylet in position for mounting to the catheter.

Referring now to FIG. 6, catheter 200 is then secured to tunneling stylet 102 by positioning first and second mounting elements 116, 118 of bifurcated segment 114 within respective lumens 206 of the catheter 200. Axial spacing of mounting elements 116, 118 (e.g., the difference in the respective lengths) facilitate insertion within the respective lumens 206 of the catheter 200. Gap 120 between first and second mounting elements 116, 118 receive septum wall 208 of catheter 200. In one embodiment, gap 120 is dimensioned whereby first and second mounting elements 116, 118 frictionally engage septum wall 208. Locking ribs 122 on the external surfaces of first and second mounting elements 116,118 frictionally engage the internals surfaces defining the lumens 206 of the catheter 200 in a manner to securely connect the catheter 200 to bifurcated segment 114. Cather portions adjacent lumens 206 may at least partially deform to receive first and second mounting elements 116, 118.

Figure 7:
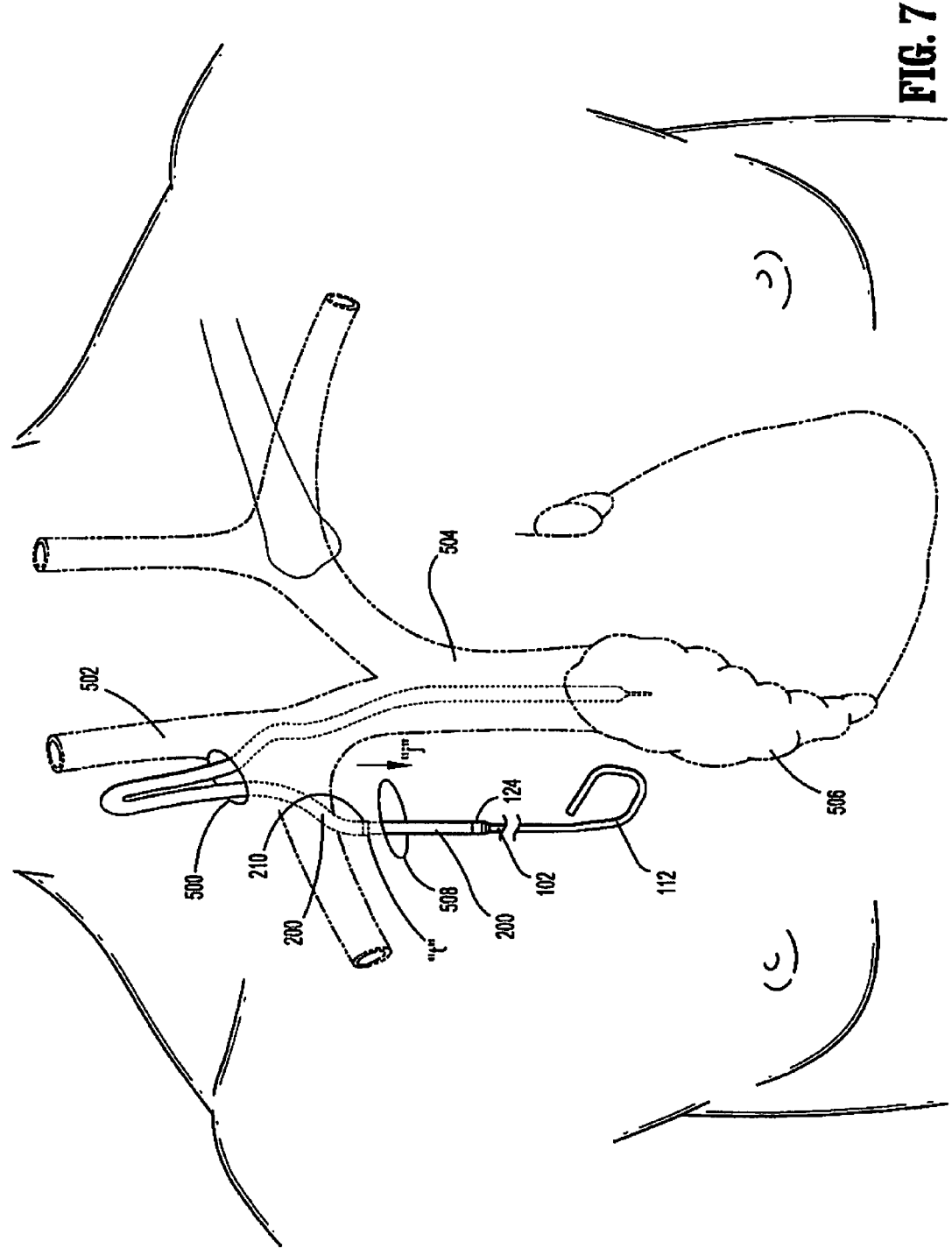
FIG. 7 is a view similar to the view of FIG. 5 further illustrating the methodology of use of the tunneling instrument.

With the catheter 200 attached, tunneling stylet 102 is drawn or pulled back toward the exit site 508 in the direction of directional arrows "j" as shown in FIG. 7. Once the trailing end of the catheter 206 is exposed from the exit site 508, the catheter 200 is released from tunneling stylet 102. The catheter 200 may then be fluidly connected to a hemodialysis machine. The clinician may employ a hub or any other suitable device to establish fluid communication between the catheter 200 and a hemodialysis machine. In FIG. 7, cuff 210 of catheter 200 is shown within the shelf "t" of the subcutaneous tunnel.

As a further alternate, it is envisioned that bifurcated segment 114 may be releasably connectable to tunneling stylet 102. A tip (not shown) may be connectable to tunneling stylet 102 during initial advancement of tunneling instrument 100 from the exit opening 508 to the venotomy site 500. Dilator element 124 may be then optionally secured to tunneling stylet 102 after the tip is removed to form the internal tissue ledge. Once the ledge is created, tunneling instrument 100 is advanced through the venotomy site 500 to remove dilator element 124 and attach the releasable bifurcated segment 114 and catheter 200 to the tunneling instrument 100. Tunneling stylet 102 may be retracted through exit site 508 in a similar manner to that described hereinabove.

Figure 8:
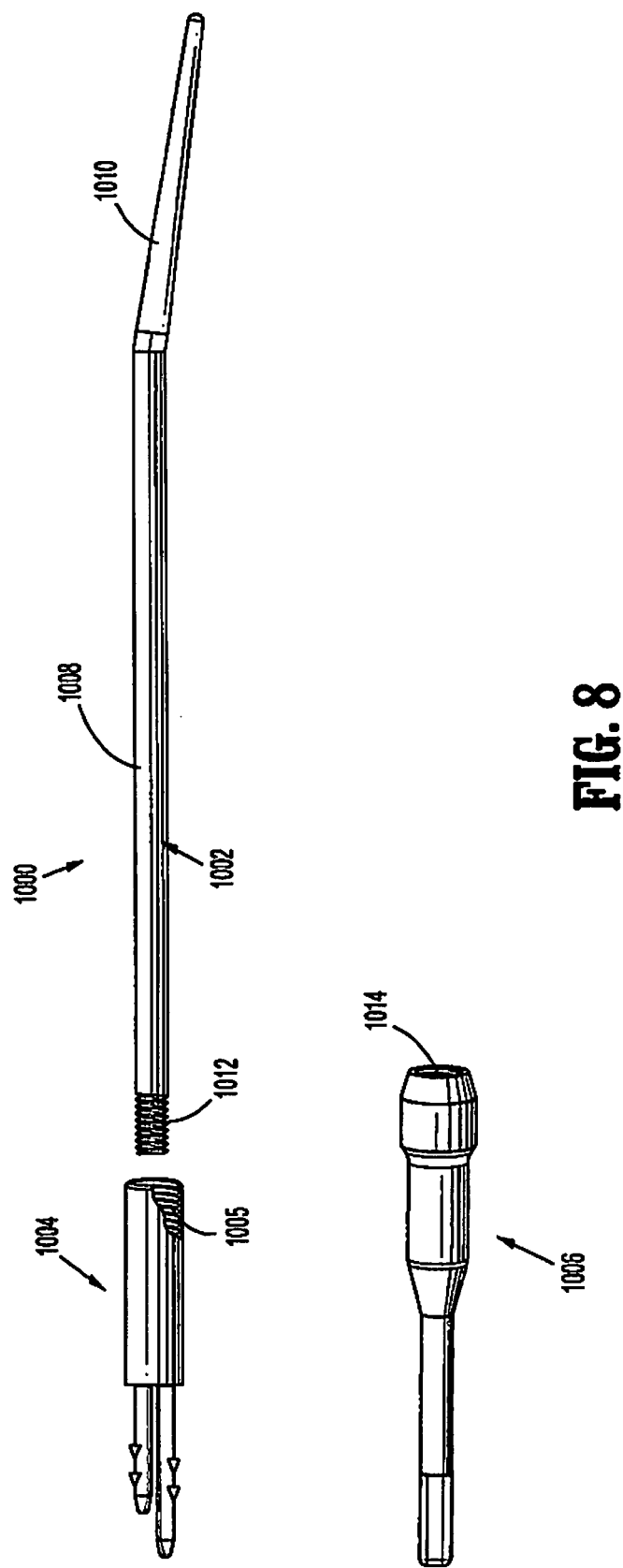
FIG. 8 is a side plan view of an alternate embodiment of the tunneling instrument illustrating the tunneling stylet, the releasable bifurcated segment and the releasable dilation member.

FIG. 8 illustrates an alternative embodiment of the present disclosure. Tunneling instrument 1000 includes tunneling stylet 1002, bifurcated segment 1004 and dilator element 1006. Tunneling stylet 1002 includes first segment 1008 defining longitudinal axis "m" and second segment 1010 extending from the first segment 1008 and obliquely arranged with respect to the longitudinal axis "m." Second or offset segment 1010 is dimensioned to facilitate passage through the subcutaneous tissue. Offset segment 1010 may incorporate any angular or arcuate arrangement suitable to facilitate insertion and/or passage through the tissue when the insertion stylet 102 is manipulated by the clinician. Offset segment 1010 defines a tapered configuration or a reduced cross-section area toward its tip as shown. First segment 1008 of tunneling stylet 1002 incorporates a threaded portion 1012 at its remote end. Bifurcated segment 1004 is substantially similar to the bifurcated segment 114 of the embodiment of FIG. 1; however, bifurcated segment 1004 is releasably mountable to tunneling stylet 1002. In one embodiment, bifurcated segment 1004 incorporates internal threads 1005 which mate with external threaded portion 1012 of tunneling stylet 1002 to releasably connect the bifurcated segment 1004 to the tunneling stylet 1002. Bifurcated segment 1004 may be devoid of external threads adjacent first and second mounting segments 116, 118. In all other respects, bifurcated segment 1004 is substantially similar to the bifurcated segment 114 of the embodiment of FIG. 1.

Dilator element 1006 is substantially similar to the dilator element 134 of the embodiment of FIG. 1, and reference is made to the foregoing description. As noted, dilator element 1006 includes an internal thread 1014 which also is releasably mateable to external threaded portion 1012 of tunneling stylet 1002 to releasably secure the dilator element 1006 to the tunneling stylet 1002.

Figure 9:
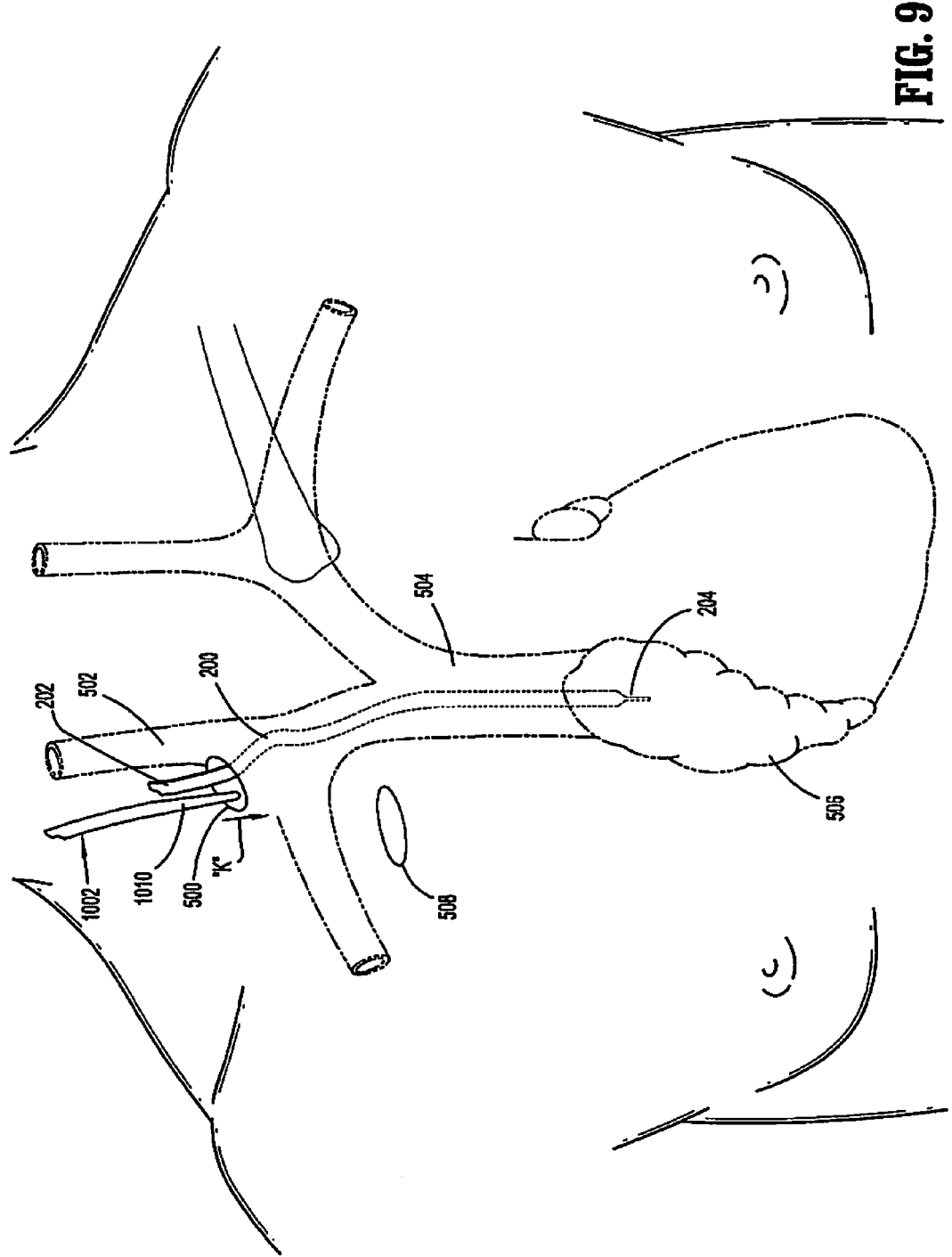
FIG. 9 is a view of the chest area of a subject illustrating a method for creating a subcutaneous tunnel for implanting a hemodialysis catheter with the tunneling instrument of FIG. 8.

The use of tunneling instrument 1000 will now be described in connection with a reverse tunneling procedure incorporating the approach from the venotomy site 500 to the exit opening 508. With reference to FIG. 9, in use, a venotomy site 500 is made and the catheter 200 is placed within the right atrium through the venotomy site 500 in the manner discussed hereinabove. A guide wire may be positioned to access the heart to facilitate insertion of the leading end 204 of catheter 200 within the heart through techniques known in the art. In accordance with one embodiment, after catheter 200 is positioned within the right atrium or other desired site as discussed hereinabove, bifurcated segment 1004 is positioned or mounted to the free or proximal end of the catheter 200 extending outwardly from the venotomy site 500. Specifically, first and second mounting segments 116, 118 are advanced to be inserted within lumens 206 of catheter 200 as shown in FIG. 10. This may seal the free end of the catheter 200 to prevent or minimize leakage of blood and aspiration of air through catheter 200 prior to tunneling. FIG. 11 illustrates bifurcated segment 1004 secured relative to catheter 200. As depicted, collar 1004c of bifurcated segment 1004 is flush against the end face of catheter 200 to substantially seal the catheter end. First and second mounting segments 116, 118 also may define a cross-sectional dimension approximating the internal dimensioning of lumens 206 to impede flow of fluids past collar 1004c and from the catheter end.

The procedure is continued by creating an exit site or opening 508 beneath the venotomy site 500 adjacent the sternum. Thereafter, dilator element 1006 is optionally mounted to tunneling stylet 1002. Second segment 1010 of tunneling stylet 1002 optionally is then introduced inside the subject through the venotomy site 500 and advanced toward the exit opening 508. As tunneling stylet 1002 is advanced through the exit opening 508, dilator element 1006 engages internal tissue beneath the venotomy site 500. An enlarged tissue tract is thereby made to create a shelf for accommodating the cuff 210 of the catheter 200 by advancing dilator element 1006 a predetermined distance through the venotomy site 500 toward the exit opening 508. The predetermined distance corresponds to the desired location of the cuff 210. Tunneling stylet 1002 is then retracted toward the venotomy site 500 and the dilator element 1006 is removed from the tunneling stylet 1002. In an alternate method, e.g., when another dilator instrument is used to create the subcutaneous shelf or when no shelf is necessary, tunneling stylet 1002 may be connected directly to bifurcated segment either before or after mounting of the bifurcated segment 1004 to catheter 200.

Figure 12:
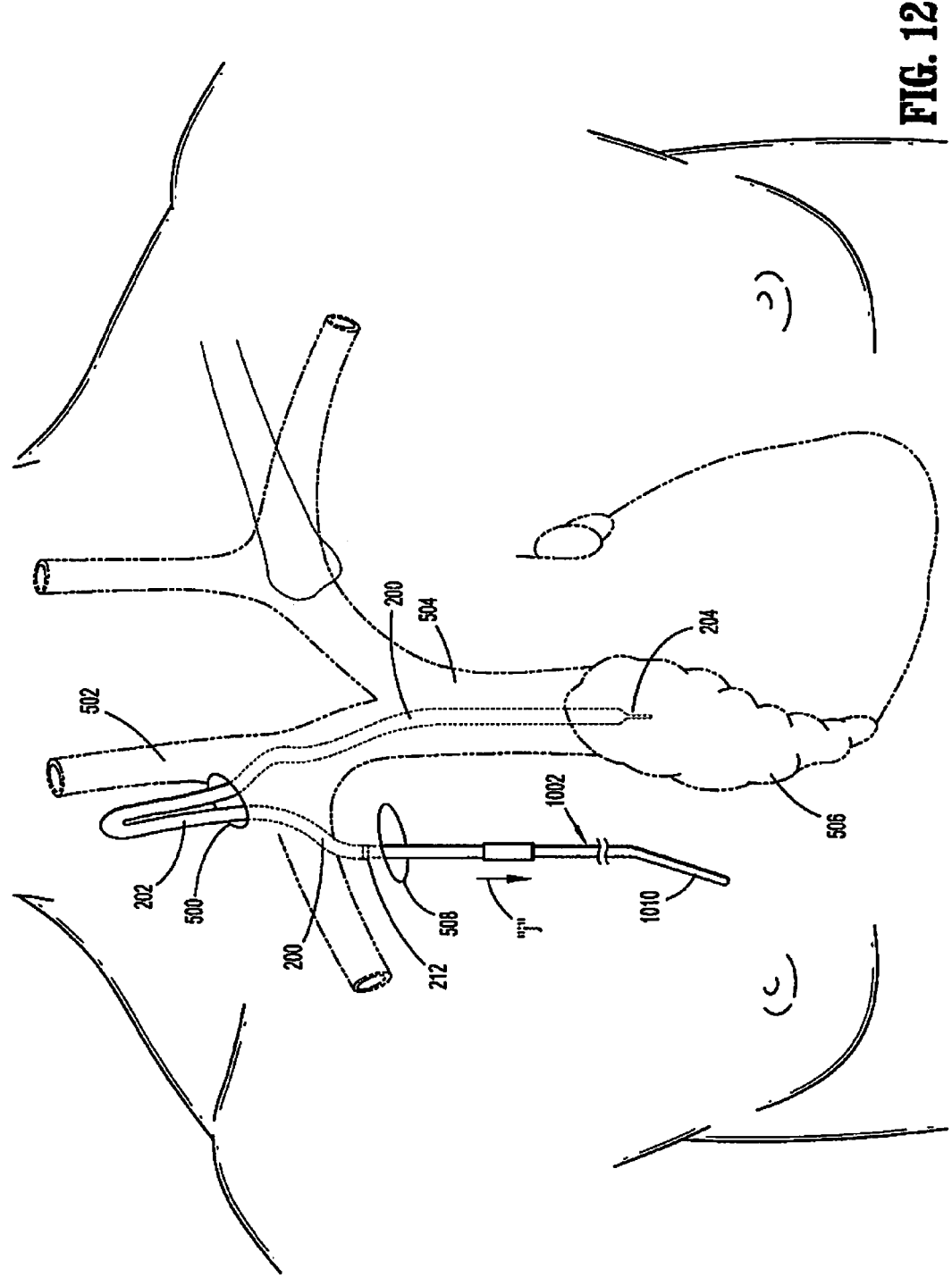
FIG. 12 is a view similar to the view of FIG. 9 illustrating the tunneling stylet advanced through an exit opening to expose the catheter end.

Referring now to FIG. 11, bifurcated segment 1004 is then mounted to insertion stylet 1002 through threaded cooperation of the threaded components. Once the catheter 200 is secured, tunneling instrument 1000 is readvanced from the venotomy site 500 through the exit opening 508 until the bifurcated segment 1004 is exposed from the exit opening 508 to expose the end of the catheter 200 as depicted in FIG. 12. The catheter 200 is removed from its mounting to tunneling instrument 1000 and fluidly connected to a hemodialysis machine via a hub or multi-tube connector assembly. In one embodiment, catheter 200 is released from its mounting to bifurcated segment 1004 by exerting a linear force on catheter 200. Alternatively, the catheter 200 is severed or cut adjacent the bifurcated segment 1004 to expose the catheter ends.

In an alternate embodiment depicted in FIG. 13, bifurcated segment 1004 may be permanently attached to tunneling stylet 1002 as described in connection with the embodiment of FIG. 1. In this embodiment, another dilator element may be used if desired to create the subcutaneous shelf.

Figure 14:
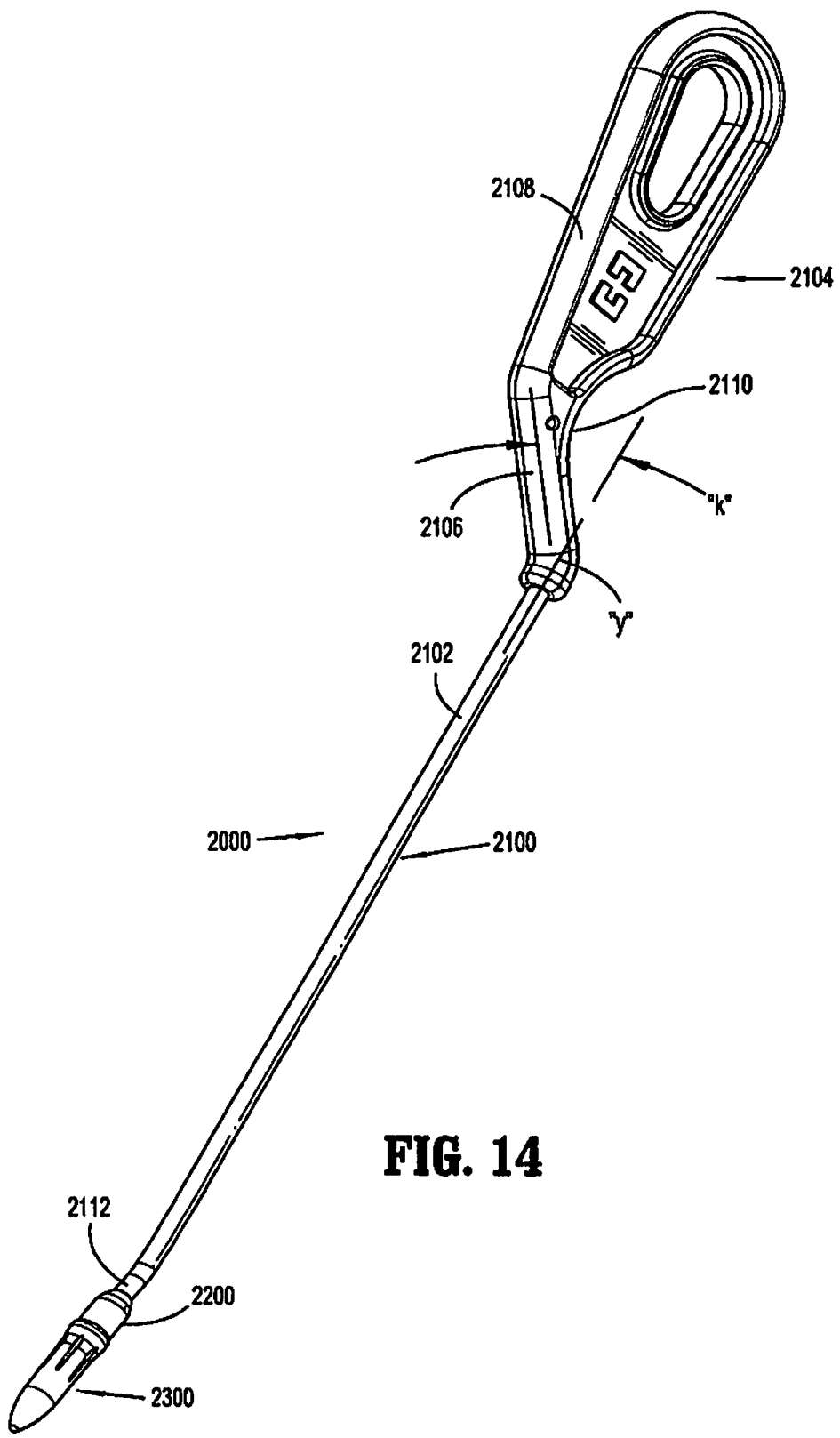
FIG. 14 is a perspective view of an alternate embodiment of the instrument of FIG. 1.
Figure 15:
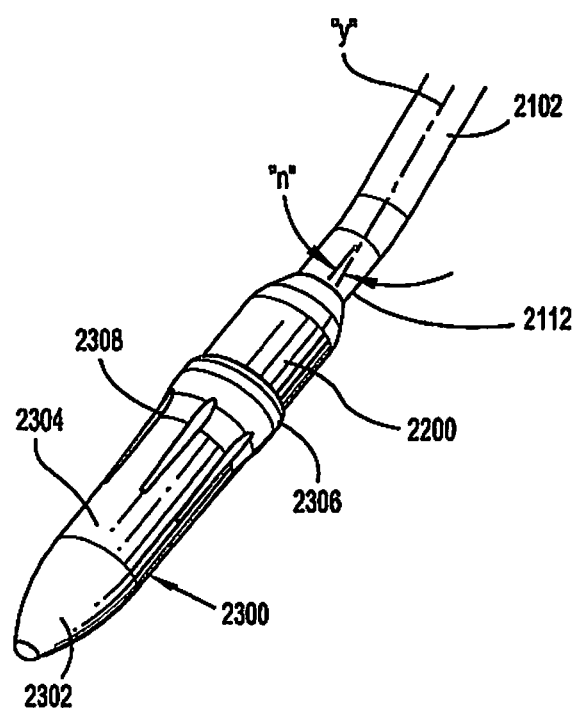
FIG. 15 is an enlarged view of the leading end of the tunneling stylet and mounted cover of the instrument of FIG. 14.

FIGS. 14-15 illustrate an alternate tunneling instrument in accordance with the present disclosure. Tunneling instrument 2000 is similar to the embodiment of FIG. 1. Tunneling instrument includes tunneling stylet 2100, catheter connector segment 2200 and cover 2300. Connector or bifurcated segment 2200 may be similar to any of the aforedescribed bifurcated segments and may or may not be releasably mounted to tunneling stylet 2100. Tunneling stylet 2100 includes stylet body 2102 and handle 2104 disposed at one end of the stylet body 2102. Handle 2104 maybe fabricated from a suitable polymeric material formed by injection molding techniques. Handle 2104 may be secured to stylet body 2102 with adhesives or the like or may be molded onto the stylet body 2102 during manufacture. Handle 2104 includes oblique segment 2106 adjacent stylet body 2102 which is arranged at an oblique angle "k" with respect to the longitudinal axis "y" of stylet body 2102, and grasping segment 2108 extending from the oblique segment 2106. Angle "k" may range from about 30 degrees to about 60 degrees. Oblique segment 2106 displaces grasping segment 2108 relative to the longitudinal axis "y". This will displace the clinician's hand from the chest area of the subject when, e.g., the clinician grasp's, with his/her palm, the grasping segment 2108. Thus, the clinician's hand is not encumbered by the chest area of the subject and/or any other instrumentation extending from the chest. Oblique segment 2106 also defines recess 2110 within which the clinician may place an index finger during manipulation of tunneling instrument 2000. Oblique segment 2106 may assume other configurations including a general U-shape, sinusoidal shape, arcuate shape, polygonal shape or other arrangements as appreciated by one skilled in the art.

Figure 14A:
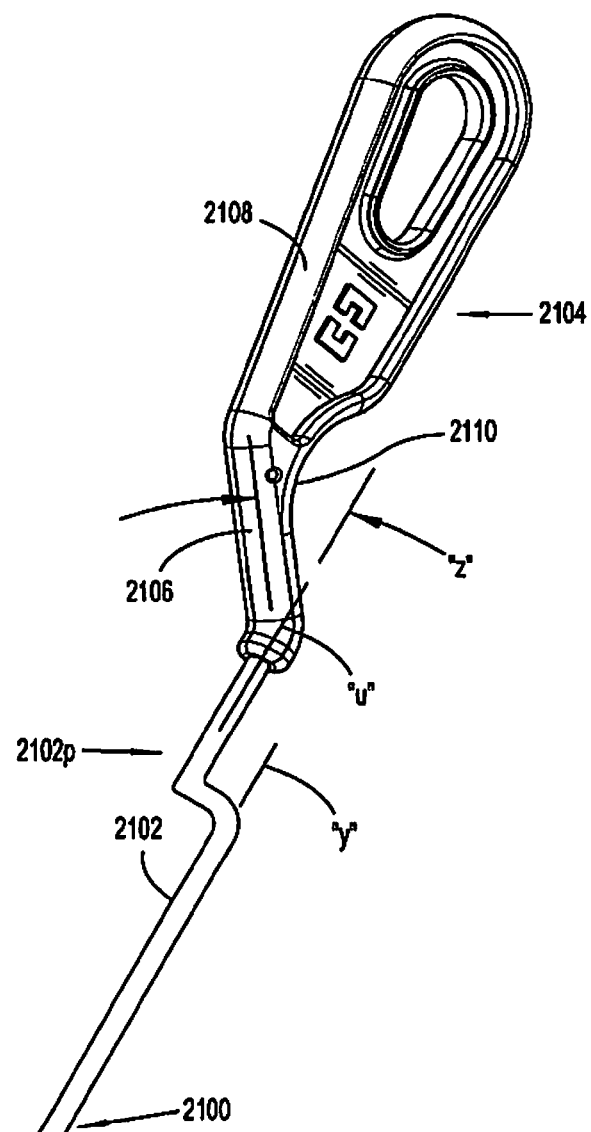
FIG. 14A is a perspective view of a further embodiment of the instrument of FIG. 1.

In the alternative, a proximal portion 2102p of the stylet body 2102 may have a curved shaped, as shown in FIG. 14A thus displacing handle 2108 both in the "x" and "z" directions as shown in FIG. 14A. This multi-plane offset arrangement may assist the clinician in steering the tunneling stylet 2100 through the subcutaneous tissue.

Tunneling stylet 2100 further defines an offset or oblique leading end 2112 which is obliquely oriented relative to the longitudinal axis of tunneling stylet at an angle "n". Angle "n" ranges from about 5 degrees to about 30 degrees relative to the longitudinal axis "y". This offset arrangement will position catheter connector segment 2200 and/or cover 2300 at an oblique arrangement with respect to the longitudinal axis "y" of tunneling stylet 2100, which may, e.g., facilitate initial insertion within the tunnel openings (e.g., the tunnel base opening or venotomy opening) in the tissue. For example, oblique leading end 2112 permits the clinician to introduce cover 2300 within the tunnel base opening at an angle thereby further displacing the clinician's hand from the chest area of the subject. This offset arrangement of oblique leading end 2112 and coupled with offset segment 2106 of handle 2104 addresses ergonomic concerns and eases manipulation of tunneling stylet 2102 through the subcutaneous tissue.

Cover 2300 may be initially releasably coupled to connector apparatus 2200 to assist in advancing tunneling stylet 2100 through tissue prior to connection to catheter 200 in a similar manner as discussed in connection with the embodiment of FIG. 1. Cover 2300 defines a generally parabolic or bullet-shaped nose 2302 which, by its geometry, is atraumatic to tissue and facilitates the dissecting of tissue during advancement to form the subcutaneous tunnel. Cover 2300 also includes cylindrical section 2304 depending from nose 2302 and collar 2306 at the end of the cylindrical section 2304. Collar 2306 defines a cross-section or diameter greater than the cross-section or diameter of cylindrical section 2304 for positioning onto connector segment 2200. Cover 2300 may include a plurality of axially extending ribs 2308 which may be peripherally or radially spaced about the exterior surface of cover 2300, and extend from cylindrical section 2304 to collar 2306. Ribs 2308 enhance gripping with fingers and facilitate rotational removal of cover 2300. Recesses defined between the ribs 2308 may receive tissue portions displaced during the tunneling procedure to facilitate advancement during formation of the tunnel. In an alternate embodiment, cover 2300 may include axial projections or ribs in lieu of, or in addition to, recesses 2308. The axial ribs may taper to increase the effective outer dimension of cylindrical section 2304 to correspond to the outer dimension of collar 2306. This arrangement may facilitate dissection of tissue to provide a more gradual transition from cylindrical section 2304 to collar 2306. Cover 2300 may be fabricated from a biocompatible polymeric material or from a suitable elastomeric material capable of slight deformation when mounted to connector segment 2200.

Although the illustrative embodiments of the present disclosure have been described herein with reference to the accompanying drawings, it is to be understood that the disclosure is not limited to those precise embodiments, and that various other changes and modifications may be effected therein by one skilled in the art without departing from the scope or spirit of the disclosure.

What is claimed is:

1. An instrument for facilitating insertion of a catheter through a subcutaneous tunnel, which comprises:
   a tunneling stylet having first and second segments, the first segment defining a longitudinal axis along at least a portion of a length thereof, the second segment being dimensioned for passage through tissue;
   a bifurcated segment releasably connectable to the first segment, the bifurcated segment including first and second elements adapted for reception within respective lumens of the catheter; and
   a dilation member releasably connectable to the first segment in the absence of the bifurcated segment, the dilation member dimensioned to generally increase an internal dimension of the subcutaneous tunnel,
   wherein the first segment of the tunneling stylet and the dilation member include cooperative threaded portions for establishing a releasable connection therebetween,
   the dilation member includes a trailing segment, an intermediate segment and a leading segment, and the dilation member defines an internal thread on an inner surface thereof configured to engage with an external thread on the first segment of the tunneling stylet, and
   the trailing segment of the dilation member includes a first tapered segment and a first cylindrical segment, and the intermediate segment includes a second tapered segment, a second cylindrical segment and a third segment, the leading segment having a cylindrical configuration.

2. The instrument according to claim 1, wherein the first and second elements of the bifurcated segment define first and second longitudinal lengths, the first longitudinal length being greater than the second longitudinal length.

3. The instrument according to claim 1, wherein the first and second elements of the bifurcated segment each include a locking rib protruding outwardly with respect to the longitudinal axis from an outer surface of the corresponding first and second elements, each locking rib being dimensioned to facilitate gripping engagement with an internal surface of respective lumens of the catheter.

4. The instrument according to claim 1, wherein the first segment of the tunneling stylet and the bifurcated segment include cooperative threaded portions for establishing a releasable connection therebetween.

5. The instrument according to claim 1, wherein the second segment of the tunneling stylet extends from the first segment of the tunneling stylet and is obliquely arranged with respect to the longitudinal axis.

6. The instrument according to claim 5, wherein the second segment of the tunneling stylet defines a tapered configuration extending in a direction away from the longitudinal axis.

7. The instrument according to claim 1, wherein the bifurcated segment has a collar from which the first and second elements of the bifurcated segment extend, the collar configured for flush engagement against an end face of the catheter.

8. The instrument according to claim 1, wherein the first and second elements of the bifurcated segment are parallel to the longitudinal axis when the bifurcated segment is connected to the first segment of the tunneling stylet.

9. A system comprising:
   a catheter defining first and second lumens;
   a tunneling stylet having first and second segments, the first segment defining a longitudinal axis along at least a portion of a length of the first segment, the second segment being dimensioned for passage through tissue;
   a bifurcated segment releasably connectable to the first segment, the bifurcated segment including first and second elements positionable within respective lumens of the catheter; and
   a dilation member releasably connectable to the first segment in the absence of the bifurcated segment,
   wherein the dilation member includes a trailing segment, an intermediate segment and a leading segment, and the dilation member defines an internal thread on an inner surface, an external surface of the first segment of the tunneling stylet defines an external thread engageable with the internal thread to releasably secure the dilation member to the tunneling stylet, and
   the trailing segment of the dilation member includes a first tapered segment and a first cylindrical segment, and the intermediate segment includes a second tapered segment, a second cylindrical segment and a third segment, the leading segment having a cylindrical configuration.

10. The system of claim 9, wherein the catheter includes a cuff circumscribing the catheter and the dilation member is sized to create a shelf in a wearer's tissue for accommodating the cuff.

* * * * *